Aug. 5, 1952 E. S. BOERNER Plant Pat. 1,117
ROSE PLANT
Filed July 11, 1951
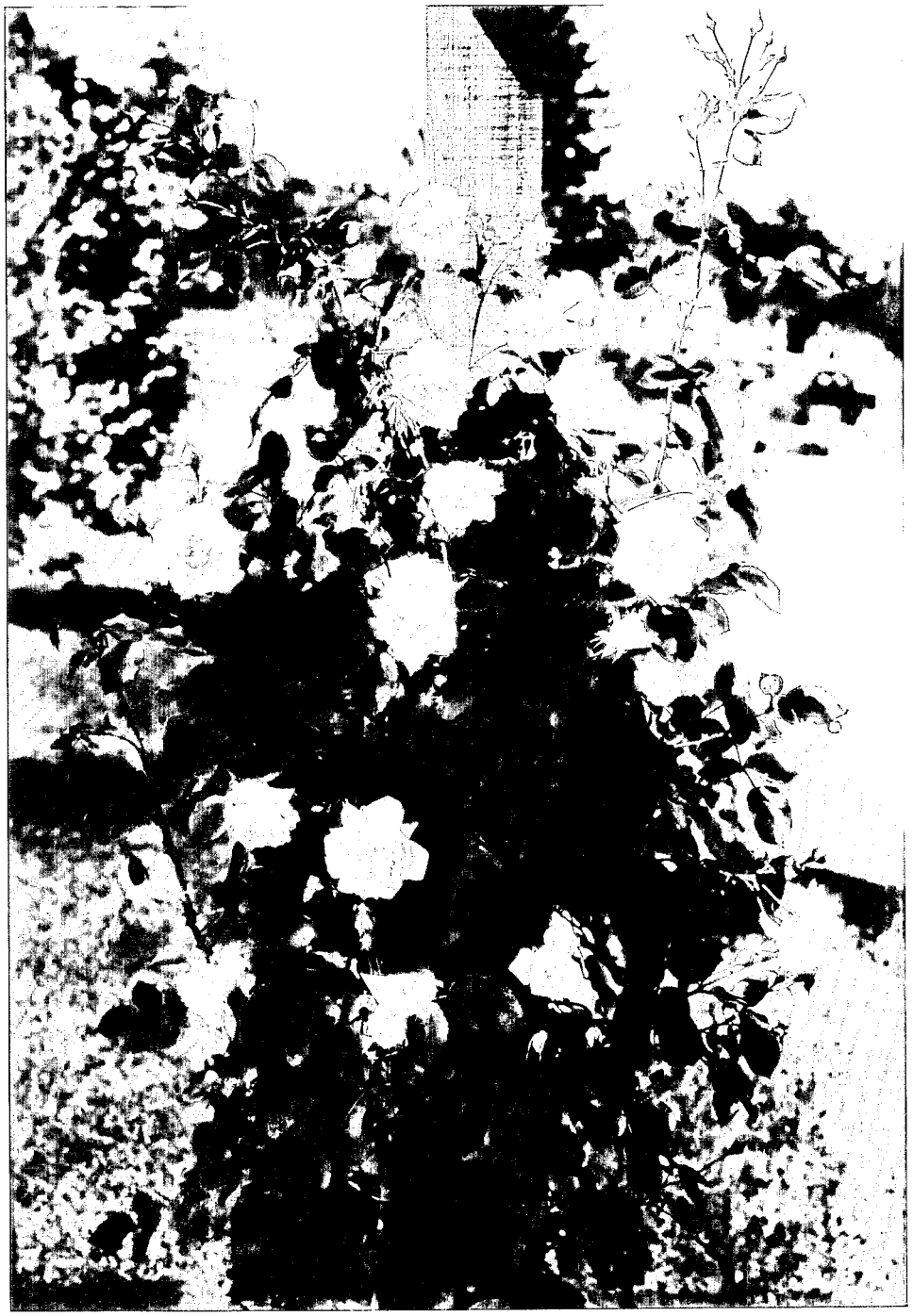
Inventor.
E. S. Boerner
By: Robert Cobb
Attorney.

Patented Aug. 5, 1952

Plant Pat. 1,117

UNITED STATES PATENT OFFICE 1,117

ROSE PLANT

Eugene S. Boerner, Newark, N. Y., assignor to Jackson & Perkins Company, Newark, N. Y., a corporation of New York Application July 11, 1951, Serial No. 236,097

1 Claim. (Cl. 47—61)

The present invention relates to a new and distinct variety of climbing rose plant which was originated by me with the primary object of producing a deeper-colored form of the variety "New Dawn" (Plant Patent No. 1), which is a very prolific re-blooming variety of climbing rose plant.

The objective of the invention was realized by crossing "New Dawn" with an unnamed and unpatented yellow hybrid tea variety, and then crossing the resulting climbing seedling with an unnamed and unpatented orange-red polyantha, this latter cross resulting in the present variety which produces flowers of a rich coral color and which have a flower form substantially like that of "New Dawn," although distinguished therefrom by being somewhat more double, with stiffer petals.

The present variety is distinguished from its parents, as well as from all other known varieties, by the following important and unique combination of characteristics and habits:

(1) The predominantly Geranium Pink general tonality of the flowers, lightly overcast with Eosine Pink;

(2) The greater number of relatively stiff petals of each flower, numbering around 60 under normal conditions, as compard with the usual 25 for "New Dawn";

(3) The longer-lasting quality of the flowers, lasting 4 to 5 days as compared with 3 days for "New Dawn;" and (4) The continous re-blooming habit of this highly colored climbing rose.

Asexual reproduction of this variety by budding at Newark, New York, and Pleasanton, California, where tests and observations were made, shows that the foregoing characteristics come true to form and are established and transmitted through succeeding propagations.

The accompanying drawing shows a specimen plant of the new variety with its flowers and foliage in various stages of development.

The following is a detailed description of the new variety, with color terminology in accordance with Ridgway's Color Standards and Nomenclature:

Parentage: Seedling.

*Seed parent.*—Climbing seedling of "New Dawn" × an unnamed yellow hybrid tea variety.

*Pollen parent.*—An unnamed orange-red polyantha.

Classification: Botanic and commercial—climber.

*Flower*

(Observations made in the fields at Newark, New York, in the middle of the month of August, at about 9:00 A. M.)

Blooming habit: Recurrent—continuous.

Bud:

*Size.*—Medium.

*Form.*—Ovoid.

*Form.*—Ovoid. Is not affected by wet or hot weather.

*Color.*—When sepals first divide—Carmine, Plate 1. When petals begin to unfurl—Spinel Pink, Plate 26. When half blown—inside of petals: Deep Rose Pink, Plate 12, lightly overcast with Eosine Pink, Plate 1; reverse of petals: Eosine Pink, Plate 1.

*Sepals.*—Smooth edge; curl back when petals begin to unfurl. Color—inside: Absinthe Green, Plate 31; outside: Biscay Green, Plate 17.

*Calyx.*—Shape — pear. Size — small. Aspect—smooth. Odor when rubbed—none. Color—Biscay Green, Plate 17.

*Peduncle.* — Length — medium. Aspect—smooth. Color—Yellowish Oil Green, Plate 5. Strength—Erect; slender.

*Opening.*—Bud opens up well. Is not affected by adverse weather conditions.

Bloom:

*Size.*—Large. Average size when fully expanded—3½ inches to 4 inches.

*Borne.*—Several together and irregular.

*Stems.*—Medium length; strong.

*Form.*—When first open—cupped. Permanence—retains its form to the end.

*Petalage.*—Very double (many petals and stamens hidden). Number of petals under normal conditions—60.

(Description made from a freshly opened bloom cut early in the morning and taken indoors or in shade.)

*Color.*—Center of flower—Geranium Pink, Plate 1. Outer petals—Eosine Pink, Plate 1, lightly overcast with Grenadine Pink, Plate 2. Base of petals (aiglet)—Marguerite Yellow, Plate 30. Inside of petals—Geranium Pink, Plate 1, lightly overcast with Eosine Pink, Plate 1. Reverse of petals—Grenadine Pink, Plate 2, lightly overcast with Eosine Pink, Plate 1. General tonality from a distance—Geranium Pink, Plate 1, lightly overcast with Eosine Pink, Plate 1.

*Discoloration.*—General tonality at end of first day—Geranium Pink, Plate 1. Second day—Geranium Pink, Plate 1, lightly overcast with Eosine Pink, Plate 1. Third day—Grenadine Pink, Plate 2, lightly overcast with Eosine Pink, Plate 1.

Petals:

*Texture.*—Thick; is not affected by wet or hot weather.

*Appearance.* — Inside — shiny; outside — satiny.

*Form.*—Oval; pointed.
*Arrangement.*—Imbricated (regularly arranged shingle-like). Petaloids in center—few; large.
*Persistence.*—Drop off cleanly.
*Fragrance.*—Moderate. Nature—tea (average hybrid tea scent).
*Lasting quality.*—On the plant—long; retains color well.

Genital organs:
*Stamens, anthers.*—Medium size; many. Color—Cream Buff, Plate 30. Arrangement—regular around styles.
*Stamens, filaments (threads).*—Medium length. Color—Alizarine Pink, Plate 13.
*Pollen.*—Color—Maize Yellow, Plate 4.
*Styles.*—Bunched; uneven length; medium length; thin.
*Stigmas.*—Color—Apricot Yellow, Plate 4.
*Ovaries.*—All enclosed in calyx.

*Plant*

Form: Climber.
Growth: Vigorous; branching.
Foliage: 5 to 7 leaflets.
*Size.*—Medium.
*Quantity.*—Normal abundance.
*Color.*—New foliage—upper side: Yellowish Oil Green, Plate 5, lightly overcast with Orange Citrine, Plate 4. Serrations and mid-rib—Victoria Lake, Plate 1; under side: Victoria Lake, Plate 1. Old foliage—upper side: Dark Cress Green, Plate 31. under side: Light Cress Green, Plate 31.
*Shape.*—Oval pointed.

*Texture.*—Upper side—leathery. Under side—smooth. Ribs and veins—ordinary.
*Edge.*—Serrated (saw-toothed).
*Serration.*—Single; small.
*Leaf stem.*—Color—Kildare Green, Plate 31. Under side—prickles.
*Stipules.*—Medium length; smooth.

Wood:
*New wood.*—Color—Yellowish Oil Green, Plate 5. Bark—smooth.
*Old wood.*—Color—Cress Green, Plate 31. Bark—smooth.

Thorns:
*Quantity.*—On main stalks from base and on laterals from stalk—ordinary.
*Form.*—Narrow base; medium length; hooked downward.
*Color when young.*—Oxblood Red, Plate 1.
*Postition.*—Irregular.

Prickles and short needles: On main stalks and on laterals—none.

I claim:

A new and distinct variety of climbing rose plant of the "New Dawn" type, characterized as to novelty by the predominantly Geranium Pink general color tonality of its flowers, lightly overcast with Eosine Pink, by the great number of its relatively stiff flower petals, by the long-lasting quality of its flowers, and by the re-blooming habit thereof, substantially as herein shown and described.

EUGENE S. BOERNER.

No references cited.